United States Patent [19]

Lau et al.

[11] Patent Number: 5,110,983
[45] Date of Patent: May 5, 1992

[54] HEXAFLUOROISOPROPYL-CONTAINING MONOMERS, PROCESS FOR THEIR PREPARATION AND THEIR USE

[75] Inventors: Jürgen Lau; Günter Siegemund, both of Hofheim am Taunus; Freimund Röhrscheid, Kelkheim/Taunus, all of Fed. Rep. of Germany

[73] Assignee: Hoechst Aktiengesellschaft, Frankfurt am Main, Fed. Rep. of Germany

[21] Appl. No.: 497,553

[22] Filed: Mar. 22, 1990

[51] Int. Cl.$^5$ ............................................. C07C 205/59
[52] U.S. Cl. .................... 562/435; 562/441; 562/468; 562/840; 562/853; 562/868; 564/156; 564/166; 564/167; 564/171; 564/315; 568/585; 568/639; 568/745
[58] Field of Search ......................... 568/639, 745, 585; 562/468, 840, 853, 441, 868, 435, 438; 564/171, 156, 158, 315, 167, 166

[56] References Cited

U.S. PATENT DOCUMENTS

| | | | |
|---|---|---|---|
| 3,355,500 | 11/1967 | Farah et al. | 568/637 |
| 4,845,183 | 7/1989 | Mueller et al. | 528/185 |
| 4,866,155 | 9/1989 | Mueller et al. | 528/173 |
| 4,925,915 | 5/1990 | Mueller et al. | 528/172 |
| 4,939,215 | 7/1990 | Mueller et al. | 525/434 |
| 4,978,790 | 12/1990 | Lau et al. | 564/315 |
| 4,992,593 | 2/1991 | Siegemund | 568/639 |

FOREIGN PATENT DOCUMENTS

| | | |
|---|---|---|
| 66298 | 12/1982 | European Pat. Off. . |
| 317883 | 5/1989 | European Pat. Off. . |
| 317940 | 5/1989 | European Pat. Off. . |
| 317942 | 5/1989 | European Pat. Off. . |

*Primary Examiner*—Richard L. Raymond
*Assistant Examiner*—Scott C. Rand

[57] ABSTRACT

Compounds of the formula I

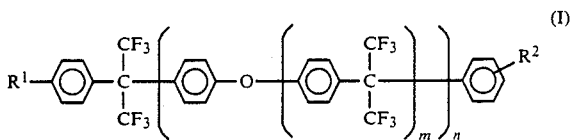

can be prepared by various process steps from 2-(4-methylphenyl)-2-hexafluoroisopropanol.

Hexafluoroisopropyl-containing monomers are important starting compounds in the preparation of linear polycarboxamides and polycarboximides.

1 Claim, No Drawings

HEXAFLUOROISOPROPYL-CONTAINING MONOMERS, PROCESS FOR THEIR PREPARATION AND THEIR USE

DESCRIPTION

The invention relates to hexafluoroisopropyl-containing monomers, process for their preparation, and their use.

Partly fluorinated aromatic diamines are valuable monomers for high temperature-resistant polycondensates, such as polyamides and polyimides.

It is known that high temperature-resistant polymers can be prepared from partly fluorinated aromatic diamines. 2,2-Bis[4-(4-aminophenoxy)phenyl]-hexafluoropropane, which contains two ether bridges and one hexafluoroisopropylidene bridge, is employed in the preparation of polyimides having favorable chemical and thermal properties (cf. U.S. Pat. No. 4,111,906). In this case, the introduction of ether bridges into polyimides increases the flexibility of the main chain, lowers the glass-transition temperature and improves the processing properties (cf. J. Polym. Sci. 74, 93 (1986)).

However, the number of available aromatic diamines which contain ether bridges and hexafluoroisopropylidene bridges is limited.

The object was therefore to prepare novel partly fluorinated aromatic diamine compounds containing ether bridges for the preparation of polyimides having favorable thermal and chemical properties.

The object is achieved by the provision of hexafluoroisopropyl-containing monomers and thus also of partly fluorinated aromatic diamino compounds, which can be prepared in several process steps starting from 2-(4-methylphenyl)-2-hexafluoroisopropanol.

The invention relates to compounds of the formula I

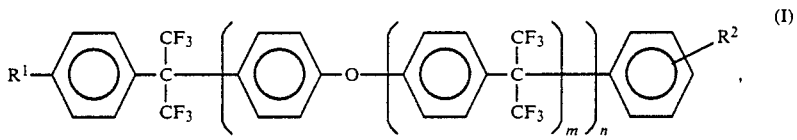

in which
m and n are zero or 1, and, if
m=zero and n=zero, then
  $R^1$ is —CH$_3$ and
  $R^2$ is —OH in the para-position, if
m=zero and n=1, then
  $R^1$ is —CH$_3$, —COOH, —COCl, —CONH$_2$ and —NH$_2$ and
  $R^2$ is —CH$_3$, —COOH, —COCl, —CONH$_2$, —NH$_2$ and —NO$_2$ in the meta- or para-position, and if
m=1 and n=1, then
  $R^1$ is —COCl, —CONH$_2$ and —NH$_2$, and
  $R^2$ is —COCl, —CONH$_2$ and —NH$_2$.

The invention furthermore relates to a process for the preparation of a compound of the formula I where m=zero and n=zero as claimed in claim 1, which comprises reacting 2-(4-methylphenyl)-2-hexafluoroisopropanol with phenol in the presence of anhydrous hydrofluoric acid to give 2-(4-hydroxyphenyl)-2-(4-methylphenyl)hexafluoropropane.

The invention also relates to a process for the preparation of compounds of the formula I where m=zero and n=1 as claimed in claim 1, which comprises 1) reacting 2-(4-hydroxyphenyl)-2-(4-methylphenyl)-hexafluoropropane with an aromatic, halogen-containing nitro compound or dinitro compound, or reacting 2-(4-methylphenyl)-2-hexafluoroisopropanol with 4-methyldiphenyl ether in the presence of anhydrous hydrofluoric acid to give 2-(4-methylphenyl)-2-[4-(4-methylphenoxy)phenyl]hexafluoropropane,
2) oxidizing a compound formed in 1) to give the carboxylic acid derivative,
3) reacting the carboxylic acid derivative with thionyl chloride to give the acid chloride,
4) reacting the acid chloride with ammonia solution to give the amide,
5) reacting the amide with dissolved sodium hydroxide and NaOCl to give the amine, and
6) catalytically reducing the nitro group in the aminonitro compound present after carrying out 5) to give the amine.

In addition, the invention relates to a process for the preparation of compounds of the formula I where m=1 and n=1 as claimed in claim 1, which comprises 1) reacting 4,4'-bis[2-(4-carboxyphenyl)hexafluoroisopropyl]diphenyl ether with thionyl chloride to give the acid chloride,
2) reacting the acid chloride with ammonia solution to give the amide, and
3) reacting the amide with dissolved sodium hydroxide and NaOCl to give the amine.

The invention also relates to the use of compounds as claimed in claim 1 for the preparation of linear polycarboxamides and polycarboximides The 12F-diamine, 4,4'-bis[2-(4-aminophenyl)hexafluoroisopropyl]diphenyl ether, is prepared starting from the 12F-dicarboxylic acid, 4,4'-bis-[2-(4-carboxyphenyl)hexafluoroisopropyl]diphenyl ether, in 3 reaction steps, the corresponding 12F-dicarboxylic acid chlorides and amides appearing as intermediates.

The 6F-diamine, 2-(4-aminophenyl)-2-[4-(4-aminophenoxy)phenyl]hexafluoropropane, is prepared by two alternative processes. In the first process, 4-methyldiphenyl ether anu 2-(4-methylphenyl)-2-hexafluoroisopropanol are reacted in the presence of anhydrous hydrofluoric acid to give the 6F-dimethyl compound, 2-(4-methylphenyl)-2-[4-(4-methylphenoxy)phenyl]hexafluoropropane, which is first converted into the 6F-dicarboxylic acid by catalytic oxidation in air, and this is finally converted, via the corresponding 6F-dicarboxylic acid chloride and amide, into 2-(4-aminophenyl)-2-[4-(4-aminophenoxy)phenyl]hexafluoropropane.

In the second process, phenol and 2-(4-methylphenyl)-2-hexafluoroisopropanol are first reacted in the presence of anhydrous hydrofluoric acid to give 2-(4-hydroxyphenyl)-2-(4-methylphenyl)hexafluoropropane. The latter is reacted with a 4-halonitrobenzene to give 2-(4-methylphenyl)-2-[4-(4-nitrophenoxy)phenyl]hexafluoropropane. The methyl compound is subsequently oxidized and converted, via the carboxylic acid chloride and carboxamide, into 2-(4-aminophenyl)-2-[4-(4-nitrophenoxy)phenyl]hexafluoropropane, from which 2-(4-aminophenyl)-2-[4-(4-aminophenoxy)- phenyl]hexafluoropropane is prepared by reducing the nitro group.

In analogy to the second process, a further 6F-diamine, 2-(4-aminophenyl)-2-[4-(3-aminophenoxy)-phenyl]hexafluoropropane, is prepared starting from 2-(4-hydroxyphenyl)-2-(4-methylphenyl)hexafluoropropane and 1,3-dinitrobenzene.

The mono- and dimethyl compounds according to the inven-tion are prepared by reacting 2-(4-methylphenyl)-2-hexafluoroisopropanol with phenol or 4-methyldiphenyl ether in the presence of anhydrous hydrofluoric acid.

The starting compound 2-(4-methylphenyl)-2-hexafluoroisopropanol is known and described in J. Org. Chem. 998–1001, 30 (1965).

The reaction temperature in the condensation process is between 80° and 180° C., preferably between 100 and 170° C. The reaction times are 24 to 90, preferably 65 to 90, hours. The molar ratio between the reactants employed is in both cases 1:5, preferably 1:1.5 to 2.5, the reactants not containing fluorine always being the components in excess. The proportion of hydrogen fluoride is related to the fluorine-containing starting compound and is at a molar ratio of 1:7 to 25, preferably 1:9 to 20. The reaction material is worked up by allowing the hydrogen fluoride to leave the reactor at about 80° C. when the reaction is complete.

The methyl compounds according to the invention are oxidized to carboxylic acids by customary stoichiometric methods using, for example, potassium permanganate, chromic acid/glacial acetic acid, dichromate/sulfuric acid or, preferably, catalytically, using molecular oxygen in the presence of a catalyst combination of the ions of cobalt, manganese and bromine, the oxidation being carried out in an acidic medium comprising at least 40% by weight of acetic acid or propionic acid, or mixtures thereof. Acetic acid is preferred due to its greater resistance to oxidative degradation.

Bromide ions are absolutely necessary for completion of the oxidation. Cobalt ions and manganese ions are employed in the ratio 3:1 to 1:3, preferably 1:1. The total of the concentrations of the two elements cobalt and manganese is 0.01 to 0.2, preferably 0.02 to 0.12 and in particular 0.04 to 0.08 g-atom/kg of the total material. The cobalt plus manganese to bromine ratio is 1:0.01 to 2, preferably 1:0.025 to 1 and in particular 1:0.05 to 0.2. In addition to the two metal ions of the catalyst, it is also possible to employ cerium ions. These catalyze the oxidation of the incompletely oxidized intermediates. Their presence increases the purity and the yield of the partly fluorinated monocarboxylic acid. The cerium ions are added to the catalyst in the cobalt ion plus manganese ion to cerium ion ratio of 1:0.02 to 2, preferably 1:0.05 to 1 and in particular 1:0.2 to 0.6. The metal ions are preferably employed in the form of their acetates.

Bromine is employed in the form of bromides, for example of alkali metals, including ammonium bromide, and those of the metals cobalt, manganese and cerium, or as a solution of hydrogen bromide in water or glacial acetic acid. It is also possible to use bromine-containing organic compounds which decompose during the oxidation and liberate bromine ions, for example tetrabromomethane.

The oxidation is carried out at temperatures of from 120° to 220° C., preferably 140° to 190° C. and in particular 155° to 180° C. The pressure in the reactor is between 5 and 40 bar, preferably between 10 and 30 bar and in particular between 14 and 20 bar.

It is favorable for the oxidation if the air required is passed into the liquid phase close to the base of the reactor and is finely distributed in the liquid phase by vigorous stirring or by special nozzles.

The starting materials used for the nitro compounds according to the invention are, for example, 2-(4-hydroxyphenyl)-2-(4-methylphenyl)-hexafluoropropane and 2-(4-carboxyphenyl)-2-(4-hydroxyphenyl)-hexafluoropropane, which are reacted with aromatic halogen-containing nitro compounds or dinitro compounds. The aromatic nitro compounds employed are preferably 4-chloronitrobenzene and 1,3-dinitrobenzene. The reaction is carried out in an organic solvent, to be precise in a dipolar aprotic solvent, such as dimethylformamide, dimethylacetamide, dimethyl sulfoxide, dimethyl sulfone, sulfolane, (tetrahydrothiophene 1,1-dioxide), or 1-methyl-2-pyrrolidinone. At least stoichiometric amounts of a basic compound, for example an alkali metal hydroxide, ammonium hydroxide, an alkali metal hydride, an alkali metal carbonate or bicarbonate or an alkaline earth metal carbonate or bicarbonate, or an alkali metal alkoxide, are employed in the reaction. The molar ratios are 1:1 to 4, preferably 1:1.1 to 2, relative to the hydroxyphenyl compound. The reaction temperature is 50° to 200° C., preferably 100° to 180° C.

The nitro compounds obtained are reduced by customary catalytic methods using hydrogenation catalysts or by stoichiometric methods, for example using tin(II) chloride/glacial acetic acid.

The catalysts employed for the catalytic reduction are, for example, platinum metals, copper, iron, cobalt, nickel, mixtures thereof or oxides of the metals mentioned, at atmospheric or elevated pressure. Palladium is preferred. The catalysts can be employed as the metal itself or in finely divided form on charcoal, barium sulfate, silica gel, aluminum and zeolite. The use of Raney nickel is also known. The reduction is carried out in an organic solvent, for example in an alcohol, such as methanol, ethanol and isopropyl alcohol, glycol, such as ethylene glycol and propylene glycol, an ether, such as diethyl ether, dioxane, tetrahydrofuran and ethylene glycol monoethyl ether, and aliphatic hydrocarbon, such as hexane and cyclohexane, an aromatic hydrocarbon, such as benzene, toluene and xylene, an ester, such as ethyl acetate and butyl acetate, a halogenated hydrocarbon, and dimethylformamide and dimethyl sulfoxide. The temperature in this reaction is between 10° and 130° C., preferably between 20° and 80° C.

For the preparation of the mono- and dicarboxylic acid chlorides and mono- and dicarboxamides according to the invention, the generally customary methods of the preparation of carboxylic acid chlorides from carboxylic acids or carboxamides from carboxylic acid chlorides are used.

For example, the reaction of carboxylic acids with thionyl chloride, phosphorus trichloride or phosphorus pentachloride, preferably with thionyl chloride, is suitable for the preparation of the carboxylic acid chlorides, which can subsequently be reacted with aqueous ammonia solution in dioxane to give the carboxamides.

The rearrangement of the carboxamides to give the amines and diamines according to the invention is carried out under the conditions of the Hofmann carboxamide degradation. In the Hofmann reaction, carboxamides are converted into amines by the action of hypohalite in the presence of bases. The hypohalite solutions employed are 5 to 30 percent by weight aqueous solutions of alkali metal hypochlorites and hypobromites, preferably an approximately 13 percent by weight sodium hypochlorite solution, in the presence of 5 to 50% by weight of a base, for example an alkali metal hydroxide or ammonium base. The carboxamide to hypohalite molar ratio is a maximum of 1:5, preferably 1:1.25, the carboxamide being suspended or completely dissolved in an organic solvent, preferably ethanol or dioxane. Organic solvents which can be used are also lower aliphatic alcohols or ethers, for example diethylene glycol dimethyl ether. To accelerate the reaction, phase-transfer catalysts, for example tetraalkylammonium salts, benzyltrialkylammonium salts, benzyltrialkylphosphonium salts, benzyltrialkylphosphonium salts, tetraalkylphosphonium salts having 1 to 6 carbon atoms in the alkyl radical, crown ethers or polyethylene glycols, may be added in amounts of from 0.1 to 20 mol-%.

The reaction temperature in the Hofmann rearrangement reaction is 10° to 150° C., preferably 70° to 90° C.

For purification of diamines, they are converted at 10° to 100° C. using acids into one of their water-soluble salts (for example the halide or bisulfate), which are inert to amino groups under the conditions used.

The diamino compounds obtained are suitable for the preparation of high temperature-resistant polycondensates, such as polyamides and polyimides.

Reaction with tetracarboxylic acid or derivatives thereof give polyimides with low dielectric constants. On the other hand, reaction with dicarboxylic acid chlorides gives polyamides.

In addition, novel monomers and oligomers can be obtained by reaction with dianhydrides. The imide monomers and oligomers obtained can be cured by addition reactions.

The diamines according to the invention are suitable for the preparation of polymeric precursors, epoxy-resin curing agents, matrix resins, laminates, films, fibers, adhesives, coatings, photoresists and moldings.

The invention is explained in greater detail by the examples.

EXAMPLE 1

Preparation of 2-(4-hydroxyphenyl)-2-(4-methylphenyl)-hexafluoropropane in accordance with the equation:

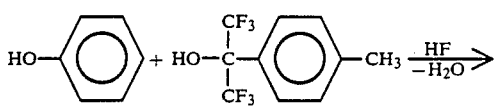

774 g (3 mol) of 2-hydroxy-2-(4-methylphenyl)-hexafluoropropane, 282 g (3 mol) of phenol and 540 g (27 mol) of anhydrous hydrogen fluoride were combined in a 2 dm³ steel autoclave and heated at 110° C. for 60 hours with stirring. The hydrogen fluoride was subsequently released and absorbed in H₂O. The autoclave residue was cooled and transferred into ice water, and the organic phase was diluted with 600 cm³ of CH₂Cl₂, washed twice with water, dried over CaCl₂ and again freed from solvent. The product was then distilled.

B.p.: 154° C/1.4, yield: 848 g = 84.6% of theory.

Analysis of the product gave the following result:

| | | | |
|---|---|---|---|
| $C_{16}H_{12}F_6O$ | calc.: C 57.48% | H 3.59% | F 34.13%; |
| (MW: 334) | found: C 56.70% | H 3.50% | F 33.80%. |

EXAMPLE 2

Preparation of 2-(4-methylphenyl)-2-[4-(4-methylphenoxy)phenyl]hexafluoropropane in accordance with the equation:

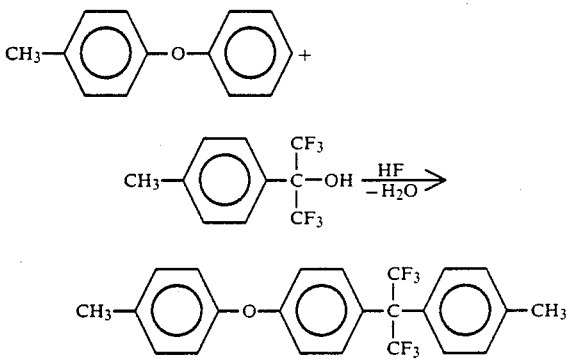

A mixture of 186 g (1.01 mol) of 4-methyldiphenyl ether, 258 g (1 mol) of 2-hydroxy-2-(4-methylphenyl)-hexafluoropropane and 180 g (9 mol) of anhydrous hydrogen fluoride were stirred at 170° C. for 65 hours in a 1 dm³ steel autoclave. The mixture was cooled to 80° C., and the hydrogen fluoride was released and absorbed in H₂O. 200 cm³ of CH₂Cl₂ were added to the residue. The organic phase was poured into ice water in order to remove residual amounts of HF, and the organic phase was separated off, washed twice with water and dried over calcium chloride. The solvent was subsequently distilled on a rotary evaporator.

The crystalline residue (434 g) was taken up in 450 cm³ of ethanol containing 20 g of activated charcoal, and the mixture was heated to the boiling point of ethanol. After the activated charcoal had been separated off, the solution was allowed to cool. The crystals weighed 207 g, yield: 48.8%. M.p.: 98.5° to 99.5° C.

Analysis of the product gave the following result:
$C_{23}H_{16}F_6O$ calc.: C 65.09% H 4.24% F 26.88%; (MW: 424) found: C 64.80% H 4.30% F 26.60%.

EXAMPLE 3

Preparation of 2-(4-carboxyphenyl)-2-[4-(4-nitrophenoxy)phenyl]hexafluoropropane in accordance with the equation:

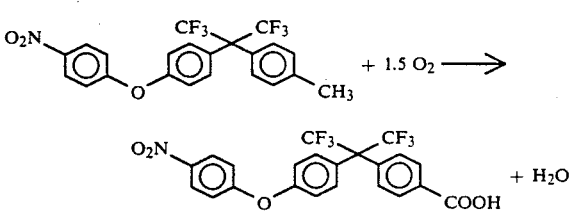

a) Oxidation

Amounts employed:
240.0 g (0.527 mol) of 2-(4-methylphenyl)-2-[4-(4-nitrophenoxy)phenyl]hexafluoropropane
2.49 g (0.01 mol) of Co(OAc)$_2$·4 H$_2$O
2.45 g (0.01 mol) of Mn(OAc)$_2$·4 H$_2$O
0.41 g (0.005 mol) of HBr, corresponding to 4.1 g of a 10 percent strength by weight HBr solution in glacial acetic acid, and
520 g of glacial acetic acid.

The mixture was heated to 185° C. under 7.5 bar. The exothermic reaction set in from about 130° C. and lasted about 25 minutes. The temperature was subsequently kept at 173° to 177° C. for a further 1 hour.

b) Work-up

The reaction solution (about 790 g) was removed from the autoclave while still hot (100° C.). The product had at that point already partly crystallized out. The crystal suspension was cooled to 22° C. with stirring, and the crystals were filtered off with suction and washed four times with 50 cm$^3$ of glacial acetic acid in each case. The yellow crystals were dried at 80° C./65 mbar in a stream of air.
Yield: 232.5 g (90.9% of theory) of yellow crystals.
M.p.: 205° to 207° C.
M.p. of the pure substance: 208° C.
Analysis of the product gave the following result:

| | | | |
|---|---|---|---|
| C$_{22}$H$_{13}$F$_6$NO$_5$ | calc.: C 54.44% | H 2.70% | N 2.89%; |
| (MW: 485.33) | found: C 54.10% | H 2.80% | N 2.80%. |

Additional carboxylic acid crystallized out on concentration of the combined filtrates to 130 g.
Yield: 4.35 g (1.7% of theory) of yellow crystals.
M.p.: 198° to 204.5° C.

EXAMPLE 4

Preparation of 2-(4-carboxyphenyl)-2-[4-(3-nitrophenoxy)phenyl]hexafluoropropane having the formula

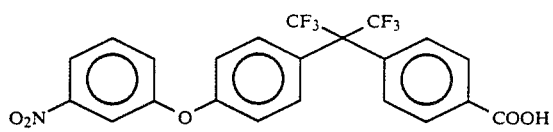

The procedure was analogous to Example 3.
Yield: 85% of theory
M.p.: 191° to 193° C.
Analysis of the product gave the following result:

| | | | |
|---|---|---|---|
| C$_{22}$H$_{13}$F$_6$NO$_5$ | calc.: C 54.44% | H 2.70% | N 2.89%; |
| (MW: 485.33) | found: C 54.30% | H 3.00% | N 2.70%. |

EXAMPLE 5

Preparation of hexafluoro-2-(4-carboxyphenyl)-2-[4-(4-carboxyphenyl)phenyl]propane in accordance with the equation:

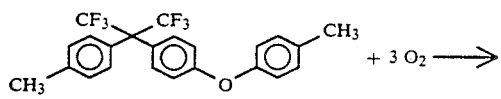

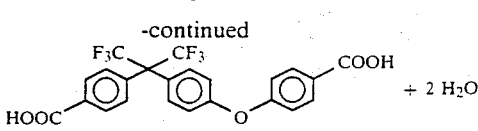

a) Reaction 225 g (0.53 mol) of hexafluoro-2-(4-methylphenyl)-2-[4-(4-methylphenoxy)phenyl]propane,
2.49 g (0.01 mol) of Co(OAc)$_2$·4 H$_2$O,
2.45 g (0.01 mol) of Mn(OAc)$_2$·4 H$_2$O,
0.41 g (0.005 mol) of HBr, corresponding to 4.1 g of a 10 percent strength by weight HBr solution in glacial acetic acid, and
525 g of glacial acetic acid were introduced into a 1 dm$^3$ glass autoclave fitted with stirrer, gas-inlet tube, thermometer and reflux condenser.

The mixture was heated to 175° C. under an oxygen pressure of 6.5 bar. The exothermic reaction set in at about 110° C. with take-up of oxygen and lasted about 45 minutes. The final temperature of 170° C. was maintained for a further 1 hour.

b) Work-up

A crystal suspension was removed from the autoclave at less than 100° C. and, after further cooling to 25° C., was filtered off with suction. The filter cake was washed four times with 50 cm$^3$ of glacial acetic acid in each case and subsequently three times with 50 cm$^3$ of water in each case. The moist product was dried at 80° C./65 mbar in a gentle stream of air.
Yield: 218.5 (95.1% of theory) of colorless crystals.
M.p.: 268° to 270° C.
Evaporation of the mother liquor to 1/7 of the original volume gave an additional 16.5 g (6.4% of theory) of dicarboxylic acid.
M.p.: 261° to 263° C.

EXAMPLE 6

Preparation of 2-(4-chlorocarbonylphenyl)-2-[4-(4-chlorocarbonylphenoxy)phenyl]hexafluoropropane 121 g of 2-(4-carboxyphenyl)-2-[4-(4-carboxyphenoxy)phenyl]hexafluoropropane were refluxed with 476 g of thionyl chloride and 0.5 cm$^3$ of dimethylformamide until evolution of gas was no longer observed. The excess thionyl chloride was removed by distillation, and the crude product was recrystallized from cyclohexane.
Yield: 122 g (94% of theory).
M.p.: 90° to 91° C.
Analysis of the product gave the following result:

| | | | |
|---|---|---|---|
| C$_{23}$H$_{12}$F$_6$Cl$_2$O$_3$ | calc.: C 52.99% | H 2.32% | Cl 13.60%; |
| (MW: 521.24) | found: C 52.70% | H 2.50% | Cl 13.40%. |

EXAMPLE 7

Preparation of 2-(4-carboxamidophenyl)-2-[4-(4-carboxamidophenoxy)phenyl]hexafluoropropane 11 g of ammonia were passed at 5° to 15° C. into a solution of 62.5 g of 2-(4-chlorocarbonylphenyl)-2-[4-(4-chlorocarbonylphenoxy)phenyl]hexafluoropropane. After 1 hour, the suspension was introduced into 3 dm$^3$ of water, and the mixture was subsequently filtered. The precipitate separated off was washed with water until neutral and, after drying, recrystallized from methanol.
Yield: 49.2 g (85% of theory), m.p.: 195° to 196° C.

Analysis of the product gave the following result:

| C$_{23}$H$_{16}$F$_6$N$_2$O$_3$ | calc.: | C 57.26% | H 3.34% | N 5.81%; |
|---|---|---|---|---|
| (MW: 482.38) | found: | C 57.00% | H 3.40% | N 5.80%. |

EXAMPLE 8

Preparation of 4,4'-bis[2-(4-carboxyphenyl)hexafluoroisopropyl]diphenyl ether 250 g of 4,4'-bis[2-(4-methylphenyl)hexafluoroisopropyl]diphenyl ether, 2.49 g of Co(OAc)$_2$·4 H$_2$O, 2.45 g of Mn(OAc)$_2$·4 H$_2$O, 0.41 g of HBr=4.1 g of a 10 percent strength by weight HBr solution in glacial acetic acid and 550 g of glacial acetic acid were introduced into a 1 dm$^3$ glass autoclave equipped with stirrer, gas-inlet tube, thermometer and reflux condenser. The mixture was heated to a maximum of 180° C. under an oxygen pressure of 7.5 bar. The exothermic reaction set in at about 130° C. with take-up of oxygen and lasted 40 minutes. The final temperature of 175° C. was maintained for a further one hour. 300 g of glacial acetic acid were distilled off from the reaction solution cooled to about 100° C., and the distillation residue was cooled to 20° C. with stirring. The crystal suspension formed was filtered off with suction. The filter cake was washed four times with 15 cm$^3$ of glacial acetic acid in each case and subsequently five times with 40 cm$^3$ of water in each case. The moist product was dried at 70° C./65 mbar in a gentle stream of air.

Yield: 211.8 g (77.6% of theory) of colorless crystals. M.p.: 238° to 240° C.

Carboxyl group content: 2.84 meq of COOH/g (calc. 2.82). Additional product precipitated from the mother liquor on addition of the washings.

Yield: 57.3 g (21.0% of theory). M.p.: 227° to 232° C.
Analysis of the product gave the following result:
C$_{32}$H$_{18}$F$_{12}$O$_5$ calc.: C54.08% H 2.53% F 32.11%; found: C 54.00% H 2.60% F 32.00%.

Preparation of 4,4'-bis[2-(4-chlorocarbonylphenyl)hexafluoroisopropyl]diphenyl ether 107 g of 4,4'-bis[2-(4-carboxyphenyl)hexafluoroisopropyl]diphenyl ether were suspended in 354 g of thionyl chloride, 0.5 cm$^3$ of dimethylformamide was added, and the mixture was refluxed until evolution of gas was no longer observed. The thionyl chloride was removed by distillation, and the crude product was recrystallized from acetonitrile.

Yield: 106 g (94.6% of theory). M.p.: 147° to 148° C.
Analysis of the product gave the following result:

| C$_{32}$H$_{16}$F$_{12}$Cl$_2$O$_3$ | calc.: | C 51.42% | H 2.15% | Cl 9.49%; |
|---|---|---|---|---|
| (MW: 747.36) | found: | C 51.00% | H 2.20% | Cl 9.50%. |

EXAMPLE 9

Preparation 4,4'-bis[2-(4-carboxamidophenyl)hexafluoroisopropyl]diphenyl ether 75 g of 4,4'-bis[2-(4-chlorocarbonylphenyl)hexafluoroisopropyl]diphenyl ether were dissolved in 300 cm$^3$ of dioxane, and 100 cm$^3$ of concentrated ammonia solution were added dropwise at 10° to 20° C. After 1 hour, the suspension was acidified (pH 4 to 5) using semiconcentrated hydrochloric acid and added dropwise to 3 dm$^3$ of ice water, and the solid was filtered off and washed with water. The dried crude product was recrystallized from acetonitrile.

Yield: 59 g (83% of theory).
Analysis of the product gave the following result:

| C$_{32}$H$_{20}$F$_{12}$N$_2$O$_3$ | calc.: | C 54.24% | H 2.85% | N 3.95%; |
|---|---|---|---|---|
| (MW: 708.50) | found: | C 54.30% | H 2.80% | N 4.10%. |

EXAMPLE 10

Preparation of 4,4'-bis[2-(4-aminophenyl)hexafluoroisopropyl]diphenyl ether 49.5 g of 4,4'-bis[2-(4-carboxamidophenyl)hexafluoroisopropyl]diphenyl ether were dissolved in 500 cm$^3$ of ethanol, and 200 cm$^3$ of 10 percent strength by weight sodium hydroxide solution and 100 g of a 13 percent strength by weight sodium hypochlorite solution were added at 10° to 20° C. The reaction mixture was refluxed for about 4 hours, cooled and filtered. The solid separated off was washed with ethanol and subsequently discarded. The mother liquor was neutralized using semiconcentrated acetic acid and evaporated. The residue was taken up in 300 cm$^3$ of ether and 200 cm$^3$ of water, the organic phase was separated off and dried over magnesium sulfate, and the solvent was removed by distillation. The pale yellow crude product was dissolved in 500 cm$^3$ of ethanol, and the impurities were removed by treatment with 2 of activated charcoal. After the ethanol had been removed, 39 g (85% of theory) of a white solid whose purity, determined by gas chromatography, was greater than 99.9%, remained. M.p.: 125.5° to 127° C.

Analysis of the product gave the following result:

| C$_{30}$H$_{20}$F$_{12}$N$_2$O | calc.: | C 55.22% | H 3.09% | N 4.29%; |
|---|---|---|---|---|
| (MW: 652.48) | found: | C 55.40% | H 3.20% | N 4.20%. |

EXAMPLE 11

Preparation of 2-(4-methylphenyl)-2-[4-(4-nitrophenoxy)phenyl]hexafluoropropane 334 g (1 mol) of 2-(4-hydroxyphenyl)-2-(4-methylphenyl)hexafluoropropane, 1.2 dm$^3$ of dimethylacetamide, 200 cm$^3$ of toluene and 44 g of sodium hydroxide were refluxed until it was no longer possible to separate off any water of reaction using a water separator. The toluene was then removed by distillation, 164.4 g (1.1 mol) of 4-chloronitrobenzene were added, and the mixture was refluxed for 48 hours. After the mixture had been cooled to about 0° C., the solid was filtered off, washed with about 100 cm$^3$ of dimethylacetamide and discarded. As much of the dimethylacetamide as possible was removed from the filtrate by vacuum distillation. The oily residue was taken up in 800 cm$^3$ of methanol, a yellow solid precipitating out. The solid was separated off and dried. After the mother liquor had been worked up, a total of 325 g (71% of theory) of a yellow solid were obtained.

M.p.: 89° to 90° C.,

Analysis of the product gave the following result:
C$_{22}$H$_{15}$F$_6$NO$_3$ (MW: 455.35) calc.: C 58.03% H 3.32% N 3.08% F 25.04% 0 10.54%; found: C 58.30% H 3.20% N 3.20% F 25.40% 0 10.50%.

EXAMPLE 12

Preparation of 2-(4-methylphenyl)-2-[4-(3-nitrophenoxy)phenyl]hexafluoropropane 334 g (1 mol) of 2-(4-hydroxyphenyl)-2-(4-methylphenyl)hexafluoropropane were dissolved in 1.5 dm³ of dimethylformamide, 276 g of potassium carbonate and 170 g (1.01 mol) of m-dinitrobenzene were added, and the mixture was refluxed for 24 hours. The dimethylformamide was subsequently removed by distillation, and the residue was recrystallized from methanol.

Yield: 219 g (48% of theory) of a brown solid.
Mp.: 65°–67° C.

Analysis of the product gave the following result:

| $C_{22}H_{15}F_6NO_3$ | calc.: C 58.03% | H 3.32% | N 3.08%; |
|---|---|---|---|
| (MW: 455.35) | found: C 57.70% | H 3.20% | N 3.20%. |

EXAMPLE 13

Preparation of 2-(4-chlorocarbonylphenyl)-2-[4-(3-nitrophenoxy)phenyl]hexafluoropropane 146 g (0.3 mol) of 2-(4-carboxyphenyl)-2-[4-(3-nitrophenoxy)phenyl]hexafluoropropane were suspended in 714 g of thionyl chloride, 1 cm³ of dimethylformamide was added, and the mixture was refluxed till evolution of gas was no longer observed. The thionyl chloride was removed by distillation, and the residue was recrystallized from acetonitrile.

Yield: 126 g (83% of theory) of a pale brown solid, m.p.: 187°–191° C.

Analysis of the product gave the following result:

| $C_{22}H_{12}F_6ClNO_4$ | calc.: C 52.45% | H 2.40% | N 2.79%; |
|---|---|---|---|
| (MW: 503.78) | found: C 52.40% | H 2.60% | N 3.10%. |

EXAMPLE 14

Preparation of 2-(4-chlorocarbonylphenyl)-2-[4-(4-nitrophenoxy)phenyl]hexafluoropropane 9.7 g (0.02 mol) of 2-(4-carboxyphenyl)-2-[4-(4-nitrophenoxy)phenyl]hexafluoropropane were suspended in 47 cm³ of thionyl chloride, a few drops of dimethylformamide were added, and the mixture was refluxed until evolution of gas was no longer observed. The thionyl chloride was removed by distillation, and the residue was recrystallized from acetonitrile.

Yield: 10 g (99% of theory) of a pale yellow solid, m.p.: 98° to 101° C.

Analysis of the product gave the following result:

| $C_{22}H_{12}ClF_6NO_4$ | calc.: C 52.45% | H 2.40% | N 2.79%; |
|---|---|---|---|
| (MW: 503.78) | found: C 52.30% | H 2.30% | N 2.50%. |

EXAMPLE 15

Preparation of 2-(4-carboxamidophenyl)-2-[4-(3-nitrophenoxy)phenyl]hexafluoropropane 11.1 g (0.022 mol) of 2-(4-chlorocarbonylphenyl)-2-[4-(3-nitrophenoxy)phenyl]hexafluoropropane were dissolved in 100 cm³ of dioxane, and 15 cm³ of concentrated ammonia solution were added at 10° to 15° C. The emulsion was stirred for 15 minutes and introduced dropwise into 800 cm³ of water. The solid was filtered off and washed with water until neutral. The dried solid was recrystallized from toluene. Yield: 8 g (75% of theory) of a pale brown solid.
M.p.: 192° to 194° C.

Analysis of the product gave the following result:

| $C_{22}H_{14}F_6N_2O_4$ | calc.: C 54.55% | H 2.91% | N 5.79%; |
|---|---|---|---|
| (MW: 484.35) | found: C 54.80% | H 3.20% | N 5.60%. |

EXAMPLE 16

Preparation of 2-(4-carboxamidophenyl)-2-[4-(4=nitrophenoxy)phenyl]hexafluoropropane 180 g (0.357 mol) of 2-(4-chlorocarbonylphenyl)-2-[4-(4-nitrophenoxy)phenyl]hexafluoropropane were dissolved in 1 dm³ of dioxane, and 150 cm³ of concentrated ammonia solution were added dropwise at 20° to 30° C. The reaction mixture was stirred for 1 hour, neutralized using hydrochloric acid (1:1) and subsequently introduced into 4 dm³ of water. The precipitate was filtered off and washed with water.

Yield: 170 g (98% of theory) of a pale brown solid.
M.p.: 208° to 210° C.

Analysis of the product gave the following result:

| $C_{22}H_{14}F_6N_2O_4$ | calc.: C 54.55% | H 2.91% | N 5.79%; |
|---|---|---|---|
| (MW: 484.35) | found: C 54.70% | H 2.70% | N 5.80%. |

EXAMPLE 17

Preparation of 2-(4-aminophenyl)-2-[4-(4-nitrophenoxy)phenyl]hexafluoropropane 4.8 g (0.01 mol) of 2-(4-carboxamidophenyl)-2-[4-(4-nitrophenoxy)phenyl]hexafluoropropane were dissolved in 150 cm³ of ethanol and 40 cm³ of dioxane. 15 cm³ of 10 percent strength by weight sodium hydroxide solution and 7.5 g of 13 percent strength by weight NaOCl solution were added to the solution, and the mixture was refluxed for 3 hours. After the reaction mixture had been cooled, the solid was filtered off, washed with 20 cm³ of ethanol and discarded. The filtrate was neutralized using dilute acetic acid and evaporated on a rotary evaporator. The residue was taken up in 50 cm³ of water and 50 cm³ of diethyl ether, and the organic phase was separated off and washed with water. The organic phase was dried over magnesium sulfate and evaporated to dryness. The crude product was recrystallized from methanol.

Yield: 2.1 g (46% of theory) of a yellow solid.
M.p.: 119° to 121° C.

Analysis of the product gave the following result:

| $C_{21}H_{14}F_6N_2O_3$ | calc.: C 55.27% | H 3.09% | N 6.14%; |
|---|---|---|---|
| (MW: 456.34) | found: C 55.50% | H 2.90% | N 6.30%. |

EXAMPLE 18

Preparation of 2-(4-aminophenyl)-2-[4-(3-nitrophenoxy)phenyl]hexafluoropropane 48 g (0.1 mol) of 2-(4-carboxamidophenyl)-2-[4-(3-nitrophenoxy)phenyl]hexafluoropropane were suspended in 800 cm³ of dioxane, and 200 cm³ of 10 percent strength by weight sodium hydroxide solution and 63 g of 13 percent strength by weight in NaOCl solution were added at about 15° C. The reaction mixture was refluxed for 3 hours, cooled to 20° C. and neutralized using dilute acetic acid. The organic phase was separated off, and the aqueous phase was extracted with 200 cm³ of ether. The organic phases were combined and evaporated on a rotary evaporator. The residue was taken up in 300 cm³ of ether and 300 cm³ of water, and the organic phase was separated off and dried over magnesium sulfate. The residue remaining after the ether had separated off was recrystallized from methanol.

Yield: 25.5 g (56% of theory) of a yellow solid.
M.p.: 79° to 83° C.
Analysis of the product gave the following result:

| $C_{21}H_{14}F_6N_2O_3$ | calc.: C 55.27% | H 3.09% | N 6.14%; |
|---|---|---|---|
| (MW: 456.34) | found: C 55.10% | H 2.70% | N 6.30%. |

EXAMPLE 19

Preparation of 2-(4-aminophenyl)-2-[4-(3-aminophenoxy)phenyl]hexafluoropropane 22.8 g (0.05 mol) of 2-(4-aminophenyl)-2-[4-(3-nitrophenoxy)phenyl]hexafluoropropane were dissolved in 600 cm³ of ethyl acetate, 1 g of palladium on charcoal was added, and the mixture was reduced in a 1 dm³ steel autoclave at about 25° C. using hydrogen (100 bar). When the take-up of hydrogen was complete, the catalyst was filtered off and all the ethyl acetate was removed. The oily, brown crude product was chromatographed over basic alumina using ethyl acetate as eluent. The principal fraction was evaporated to dryness, giving 18 g of a highly viscous, pale yellow residue. 9.5 g of the pale yellow residue were suspended in 100 cm³ of hydrochloric acid (1:1), and 400 cm³ of water were added at the boiling point. The turbid solution was treated twice at the boiling point with 5 g of activated charcoal in each case. The clear, colorless solution was cooled to 20° C., a white solid precipitating out. The suspension was adjusted to a pH of 8-9 under a protective gas (nitrogen) using dilute ammonia solution. The solid was, under a protective gas, filtered off, washed with water and dried.

Yield: 5.8 g (52% of theory) of a grey-white solid.
M.p.: 55° to 59° C. (purity according to GC: 99.1%).
Analysis of the product gave the following result:
$C_{21}H_{16}N_2O$ (MW: 426.36) calc.: C 59.15% H 3.78% N 6.57% F 26.74%; found: C 59.00% H 3.50% N 6.60% F 26.60%.

EXAMPLE 20

Preparation of 2-(4-aminophenyl)-2-[4-(4-aminophenoxy)phenyl]hexafluoropropane 48 g (0.1 mol) of 2-(4-carboxamidophenyl)-2-[4-(4-carboxamidophenoxy)phenyl]hexafluoropropane were dissolved in 2 dm³ of ethanol, 1 cm³ (0.002 mol) of tricaprylylammonium chloride was added, and 400 cm³ of 10 percent strength by weight sodium hydroxide solution and 168 g of 13 percent strength by weight NaOCl solution were added at 0° to 5° C. The reaction mixture was refluxed for 22 hours, cooled to about 25° C. and filtered. The filtrate was concentrated to about 400 cm³ in a water-pump vacuum. The two-phase residue was taken up in 300 cm³ of ether, the aqueous phase was extracted with 200 cm³ of ether, and the combined organic phases were washed with water and dried over magnesium sulfate. After the ether had been removed by distillation, the residue was suspended in 100 cm³ of hydrochloric acid (1:1), and the suspension was diluted with 1.5 dm³ of water and treated, at the boiling point, three times with 3 g of activated charcoal in each case. The clear solution was cooled to 25° C., a white solid precipitating out. The suspension was saturated with nitrogen and adjusted to a pH of 8 to 9 under nitrogen using dilute ammonia solution. The solid was filtered off under nitrogen on a reverse frit, washed with water and dried.

Yield: 31 g (73% of theory) of a white solid.
M.p.: 85° to 87° C. (purity according to GC: 99.9%).
Analysis of the product gave the following result:

| $C_{21}H_{16}F_6N_2O$ | calc.: C 59.15% | H 3.78% | N 6.57%; |
|---|---|---|---|
| (MW: 426.36) | found: C 58.70% | H 3.60% | N 6.70%. |

We claim:
1. A compound of the formula I

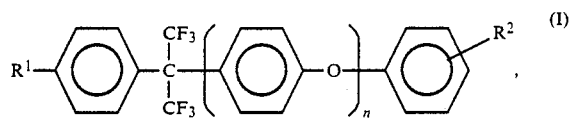

in which n is zero or 1, and, if
n = zero, then
  R¹ is —CH₃ and
  R² is —OH in the para-position, and if
n = 1, then
  R¹ is —CH₃, —COOH, —COCl, —CONH₂ or —NH₂ and
  R² is —CH₃, —COOH, —COCl, —CONH₂, —NH₂ or —NO₂ in the meta- or para-position.

* * * * *